United States Patent [19]

Metz et al.

[11] 4,282,385

[45] Aug. 4, 1981

[54] HYPERACIDIC SOLID METAL LACTATES AND PROCESS FOR PRODUCING SAME

[75] Inventors: Ulrich Metz, Seebruck, Austria; Horst Michaud, Trostberg, Fed. Rep. of Germany

[73] Assignee: SKW Trostberg Aktiengesellschaft, Trostberg, Fed. Rep. of Germany

[21] Appl. No.: 33,000

[22] Filed: Apr. 25, 1979

[30] Foreign Application Priority Data

May 12, 1978 [DE] Fed. Rep. of Germany ....... 2820942

[51] Int. Cl.$^3$ .............................................. C07C 59/08
[52] U.S. Cl. ...................................................... 562/589
[58] Field of Search ......................................... 562/589

[56] References Cited

U.S. PATENT DOCUMENTS

| | | | |
|---|---|---|---|
| 2,557,283 | 6/1951 | Hansen | 562/589 |
| 2,710,789 | 6/1955 | Boeri | 562/589 |

FOREIGN PATENT DOCUMENTS 266607  3/1927  United Kingdom ..................... 562/589

*Primary Examiner*—Paul J. Killos

[57] ABSTRACT

Novel hyperacid solid metal lactates containing up to about twenty moles of lactic acid per mole a neutral metal lactate are produced by reacting an aqueous solution of lactic acid containing up to about 0.5 percent polylactic acids with a suitable metal compound. Such lactates have the formula $Me(C_3H_5O_3)_x (C_3H_6O_3)_n$ wherein n represents a number from 4 to 12 and x corresponds to the valence of the metal Me, and are useful in the food industry as substitutes for liquid lactic acids in the making of bread and beverages.

12 Claims, No Drawings

HYPERACIDIC SOLID METAL LACTATES AND PROCESS FOR PRODUCING SAME

BACKGROUND OF THE INVENTION

Liquid lactic acid is used as a natural acid in the food industry, particularly as an acidulant in the making of bread and the preparation of beverages, for acidification purposes and to improve the shelf life of foods. Its "round", fine, acid taste makes it particularly suitable for this application. However, because elaborate preparations must be made when measuring out the liquid lactic acid, it cannot be used extensively despite the advantageous taste properties. For processing reasons, naturally-solid crystalline citric acid is preferred even though it is stronger and more acid-tasting.

The natural calcium salt of lactic acid, $Ca(C_3H_5O_3)_2$, has the property of adding further acids and hence forming overacidified or hyperacidified salts. Hyperacidified addition compounds of calcium lactate have been described in a number of previous publications, for example in German Reich Pat. No. 346,521, German Reich Pat. No. 414,171, and U.S. Pat. No. 2,046,610. However, it has not proved possible, thus far, to manufacture compounds containing more than 3 moles of free lactic acid per mole of calcium lactate. As a rule, only 1-2 moles of lactic acid are bonded to the known hyperacidified salts by the addition process. Calcium lactates with more than 2 moles of added lactic acids are hygroscopic, as described in German Reich Pat. No. 414,171. According to the known process, hyperacidified calcium lactates are obtained by the direct action of at least 90% lactic acid solutions on lime, calcium carbonate, or neutral calcium lactate, or they are produced in an organic solvent reaction medium according to U.S. Pat. No. 2,046,610, whereby water must be completely or largely excluded.

In the known powdered hyperacidified calcium lactates, at most 45% of the free lactic acid is available for acidification purposes. Hence, for cost reasons, this acid in its solid form is not competitive with other acidifiers and can be used economically only in exceptional cases.

Being an α-hydroxy acid, lactic acid is in equilibrium with its esters, the so-called polylactic acids with various chain lengths, or its lactide; this equilibrium is dependent on both concentration and time. Solutions having lactic acid concentrations of 90%, or more, produce polylactic acid contents of over 40% (see C. H. Holten, Lactic Acid 1971, p. 24). Hence, all calcium lactates, which are manufactured from concentrated lactic acid solutions, contain larger proportions of polylactic acids with unknown chain lengths. These products manufactured according to German Reich Pat. Nos. 346,521 or 414,171 are not uniform by comparison with the calcium trilactates and calcium tetralactates produced according to U.S. Pat. No. 2,046,610. Moreover, due to the high degree of esterification of the lactic acid, determined by their polylactic acids and lactide, such calcium lactates also have a significantly lower content of free lactic acid available for acidification purposes than is the case in the true addition compounds produced from lactic acid and neutral calcium lactate.

However, all known manufacturing processes are elaborate and expensive. Hence, despite special purifying operations, only powdered non-hygroscopic products with a maximum of 2-3 moles of free acid can be produced.

The desirability of producing solid, non-caking lactates with a high free lactic acid content therefore is clear.

SUMMARY OF THE INVENTION

It has been discovered according to the present invention that metal lactates having the general formula $M(C_3H_5O_3)_x \cdot (C_3H_6O_3)_n$, in which n is a number between 1 and 20 inclusive and x is the valence of the metal M, are solid lactates having a high content of free or available lactic acid. Preferably, n is a number between 4 and 12, inclusive and the lactates are noncaking, free-flowing, fine powders. Metal lactates in which Me is lithium or an alkaline-earth metal are preferred and calcium lactates are particularly preferred.

The lactates according to the invention, surprisingly, can be made by reacting aqueous lactic acid solutions, which are practically free of lactic acid esters, with a metal compound suitable for lactate formation in the quantity corresponding stoichiometrically to the desired product, whereby substances other than calcium compounds prove to be usable. In particular, the hyperacidified calcium lactates produced according to the present invention in which n is equal to or less than 12, as well as other lactates produced according to the invention, accumulate in the form of a crystalline powder and are not hygroscopic.

Suitable reactive metal compounds are, for example, oxides, hydroxides, carbonates, or other lactates. Calcium oxide, calcium hydroxide, calcium carbonate, neutral calcium lactate, or hyperacidified calcium lactates with up to 4 moles of lactic acid are particularly suitable for use as reactive calcium compounds.

Lactic acid which is practically free of its esters is obtained simply by heating dilute aqueous lactic acid solutions. With hydrolysis of the esters, hydrolyzed aqueous lactic acid is suitable for use according to the process of the present invention in concentration up to a maximum concentration of 50% by weight. Residual amounts of polylactic acids, up to 0.5% by weight of the hydrolysis solution, have no distorting effect on the properties of the hyperacidified metal lactates produced according to the present invention.

It is advantageous to effect the hydrolysis of the lactic acid ester by refluxing for several hours, preferably using aqueous lactic acid having a concentration of 20-30% by weight. If necessary, the hydrolysis reaction can be carried out under pressure at a correspondingly higher temperature, and this considerably accelerates the hydrolysis of the lactic acid ester. The hyperacidified lactates made from the lactic acid which is pretreated according to the process of the present invention, particularly the calcium lactates, have a pleasant, acid taste, as lactic acid has, are practically free of polylactic acids and lactide, and provide a free or available lactic acid content for acidification purposes of up to 80% by weight, or more, based upon the weight of the hyperacidic lactate.

The amount of lactic acid capable of acidification contained in the hyperacidified solid calcium lactate with a general formula $Ca(C_3H_5O_3)_2 \cdot (C_3H_6O_3)_n$ with n equal to or greater than 10 therefore corresponds to the concentration of the 80% commercial product which is liquid at the present time, or is even superior in its effect.

According to the process of the present invention, the aqueous metal lactate solutions obtained by the present reaction are dried in a vacuum in the shortest possible time. Particularly suitable for this purpose are thin-layer evaporators, roller driers, and paddle-or-shovel driers of the "Drais" type, as well as other devices permitting rapid evaporation of the solvent in a vacuum. Part of the dry compound is obtainable in the crystalline form depending on the metal and lactate content.

Hyperacidified calcium lactates produced according to the present invention, using more than 12 moles of added lactic acid (n greater than 12) per mole of neutral calcium lactate, take on first a crumbly then a freely caking consistency as the concentration of free lactic acid increases.

If the upper limit of N=20 is exceeded, products of a viscous oily consistency are obtained. Hence, they do not have the good dispensability essential for practical application.

The products according to the invention assume the pourable form with a lower moisture content (about 1-2%); with further drying, breaking up and grinding become unnecessary. The products obtained in this way have good water solubility.

EXAMPLE 1

Calcium hexalactate $Ca(C_3H_5O_3)_2 \cdot (C_3H_6O_3)_4$ 30 kg of 80% synthetic lactic acid are dissolved in 66 kg of water and refluxed for 15 hours. Next, 4.4 kg of calcium carbonate are added to the approximately 25% solution of lactic acid at a temperature of about 70° C., while stirring, and the clear solution is finally dried in a thin-layer evaporator at about 80° C. and 25-50 torr vacuum. 25.4 kg of pourable calcium hexalactate are obtained, corresponding to 98.9% of the theoretical quantity.

The distillate still contains 0.4% lactic acid and is recycled to the process to dilute the 80% lactic acid.

The calcium hexalactate contains 1.8% water and has a melting point of 145°-149° C.; the polylactic acid concentration, expressed as lactic acid, amounts to 2.3%.

EXAMPLE 2

Calcium nonalactate $Ca(C_3H_5O_3)_2 \cdot (C_3H_6O_3)_7$ 12 kg of 88% fermentation lactic acid are diluted with 26 kg of water and hydrolyzed for 3 hours under pressure at 150° C. The solution, which has a faint yellow color, is treated with 0.73 kg of calcium oxide at about 80° C., filtered to remove small quantities of inorganic impurities, and dried in a thin-layer evaporator as described in Example 1.

10.9 kg of white, pourable calcium nonalactate are obtained corresponding to 98.5% of the theoretical quantity. The product contains 1.2% water and 2.7% polylactic acids, expressed as lactic acid, and has a melting point of 142°-144° C.

EXAMPLE 3

Calcium lactate with the formula $Ca(C_3H_5O_3)_2 (C_3H_6O_3)_{10.8}$ 2.5 kg of 80% synthetic lactic acid are mixed with 2.5 kg of water, refluxed for 18 hours, and stirred into a solution of 0.16 kg of calcium hydroxide at a temperature of about 70° C., and subsequently dried in a laboratory thin-layer evaporator. The operating temperature is 60°-70° C. at 12-15 torr vacuum produced by an aspirator.

2.03 kg of calcium lactate with the above formula are obtained. The product has a melting point of 139°-145° C., still contains 2% water, and has a polylactic acid concentration of 1.2% expressed as lactic acid.

The distillate contains about 0.3% lactic acid distilled with water according to its vapor pressure.

EXAMPLE 4

Calcium tetradecalactate $Ca(C_3H_5O_3)_2 \cdot (C_3H_6O_3)_{12}$ 2.5 kg of 80% synthetic lactic acid are mixed with 6.5 kg of water, refluxed for 15 hours, and dissolved in the solution of 0.4 kg neutral calcium lactate with a temperature of 50° C. The clear solution is evaporated in a laboratory thin-layer evaporator as in Example 1. The operating temperature at 12-15 torr amounts to 70°-80° C.

2.37 kg of calcium tetradecalactate are obtained, corresponding to 98.6% of the theoretical quantity. The product has a melting point of 133°-138° C. and contains 1.9% water. The polylactic acid concentration expressed as lactic acid is 2.4%.

EXAMPLE 5

Lithium tetralactate $Li(C_3H_5O_3) \cdot (C_3H_6O_3)_3$ 2880 g of 25% hydrolyzed synthetic lactic acid are stirred into 83.8 g of lithium hydroxide . H$_2$O. The resulting clear solution is dried in the laboratory thin-layer evaporator according to the process described in Example 1 at 12-15 torr and 80° C. 896 g of a pourable crystalline lithium tetralactate with a melting point of 250°-255° C. are obtained.

EXAMPLE 6

Magnesium octalactate $Mg(C_3H_5O_3)_2 \cdot (C_3H_6O_3)_6$ 10.07 g of magnesium oxide are dissolved at 60°-70° C. in 720 g of 25% synthetic lactic acid, the solution is diluted to about 1000 g with water to prevent crystallization and evaporated until dry as in Example 1 in the laboratory thin-layer evaporator at 12-15 torr and 80° C. The magnesium octalactate obtained has a crumbly and easily caked consistency. 179.5 g are obtained.

EXAMPLE 7

Magnesium tetralactate $Mg(C_3H_5O_3)_2 \cdot (C_3H_6O_3)_2$ 20.1 g of magnesium oxide are dissolved at 60°-70° C. in 720 g of 25% synthetic lactic acid; the solution is diluted to about 800 g, and the further procedure is according to Example 6. A crystalline magnesium tetraclactate melting at 300° C. is obtained. The yield is 196 g.

We claim:

1. A hyperacidic, non-hygroscopic, non-caking, free-flowing solid metal lactate having the formula:

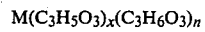

$M(C_3H_5O_3)_x(C_3H_6O_3)_n$ wherein x corresponds to the equivalence of the metal M, M is selected from the group consisting of lithium and alkaline earth metals, and n is a number from 4 to 12.

2. A crystalline non-hygroscopic calcium lactate according to claim 1 having the formula:

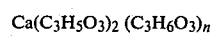

$Ca(C_3H_5O_3)_2 (C_3H_6O_3)_n$ wherein n represents a number from 4 to 12.

3. A hyperacidic, solid lithium lactate according to claim 1 having the formula:

$$Li(C_3H_5O_3)(C_3H_6O_3)_n$$

wherein n represents a number from 4 to 7.

4. A hyperacidic, solid magnesium lactate according to claim 1 having the formula:

$$Mg(C_3H_5O_3)_2(C_3H_6O_3)_n$$

wherein n represents a number from 4 to 8.

5. A process for the production of hyperacidic, non-hygroscopic, non-caking, free-flowing solid metal lactates comprising:
(a) providing a dilute aqueous solution of lactic acid having a maximum concentration of 50% and a maximum residual polylactic acid content of 0.5% by weight of said solution;
(b) reacting x plus n moles of said dilute solution with one mole of a metal compound selected from the group consisting of compounds of lithium and alkaline earth metals in a quantity corresponding stoichiometrically to the desired hyperacidic metal lactate to be formed; and
(c) removing the water solvent to produce a hyperacidic solid metal lactate having the formula $M(C_3H_5O_3)_x(C_3H_6O_3)_n$ wherein n is a number from 4 to 12 and x corresponds to the equivalence of the metal M.

6. A process according to claim 5 in which the aqueous solution of lactic acid comprises a hydrolized aqueous lactic acid solution containing an acid concentration of at most 50% by weight.

7. A process according to claim 6 in which the aqueous solution of lactic acid comprises a hydrolized aqueous solution containing lactic acid content of 20 to 30% by weight.

8. A process according to claim 5 in which the metal compound is selected from the group consisting of oxides, hydroxides, carbonates and neutral lactates.

9. A process according to claim 5 in which the metal compound is selected from the group consisting of calciumoxide, calciumhydroxide, calciumcarbonate, calciumlactate, calciumtrilactate and calciumtetralactate.

10. A process according to claim 5 in which the solvent is removed by evaporation at 10–50 TORR and 40° to 90° C.

11. A process according to claim 10 in which evaporation occurs at a temperature of from 60° to 80° C.

12. A process according to claim 10 in which evaporation occurs within a thin film apparatus or drum dryer under vacuum.

* * * * *

UNITED STATES PATENT AND TRADEMARK OFFICE
CERTIFICATE OF CORRECTION

PATENT NO. : 4,282,385
DATED : August 4, 1981
INVENTOR(S) : Ulrich Metz and Horst Michaud It is certified that error appears in the above-identified patent and that said Letters Patent are hereby corrected as shown below:

Line 2 of Abstract, after the word mole "a" should be --of--; Lines 6 and 8 of Abstract, "Me" should read --M--; Column 3, Line 13, "N" should be --n--.

Signed and Sealed this

First Day of December 1981

[SEAL]

Attest:

Attesting Officer

GERALD J. MOSSINGHOFF

Commissioner of Patents and Trademarks

REEXAMINATION CERTIFICATE (559th)

United States Patent [19]

Metz et al.

[11] B1 4,282,385

[45] Certificate Issued    Aug. 19, 1986

[54] HYPERACIDIC SOLID METAL LACTATES AND PROCESS FOR PRODUCING SAME

[75] Inventors: Ulrich Metz, Seebruck, Austria; Horst Michaud, Trostberg, Fed. Rep. of Germany

[73] Assignee: SKW Trostberg Aktiengesellschaft, Trostberg, Fed. Rep. of Germany

Reexamination Request:
No. 90/000,300, Dec. 3, 1982

Reexamination Certificate for:
Patent No.:    4,282,385
Issued:    Aug. 4, 1981
Appl. No.:    33,000
Filed:    Apr. 25, 1979

Certificate of Correction issued Dec. 1, 1981.

[30]    Foreign Application Priority Data
May 12, 1978 [DE]    Fed. Rep. of Germany ....... 2820942

[51] Int. Cl.$^4$ ............................................. C07C 59/08
[52] U.S. Cl. .................................................... 562/589
[58] Field of Search ........................................ 562/589

[56]      References Cited

FOREIGN PATENT DOCUMENTS

| | | | |
|---|---|---|---|
| 0346521 | 1/1922 | Fed. Rep. of Germany | 562/589 |
| 0593657 | 3/1934 | Fed. Rep. of Germany | 562/589 |
| 0745526 | 4/1944 | Fed. Rep. of Germany | 562/589 |
| 7106959 | 11/1972 | Netherlands | 562/589 |

OTHER PUBLICATIONS

Josef Schormuller "Lehr der Lebensmittelchemie" Springer Verlag (1961) p. 598.
Haussler, A.; Deutsche, Lebensmittel Rundschau 3 (Feb. 15, 1940) 11–14.
Schormüller; J.; Lehrbuch der Rebensmittelchemie (Apr. 27, 1969) p. 598.
Holten, Lactic Acid, Verlag Chemie (1971) pp. 199–203 and 211–216.

*Primary Examiner*—Paul J. Killos

[57]      ABSTRACT

Novel hyperacid solid metal lactates containing up to about twenty moles of lactic acid per mole of neutral metal lactate are produced by reacting an aqueous solution of lactic acid containing up to about 0.5 percent polyactic acids with a suitable metal compound. Such lactates have the formula $M(C_3H_5O_3)_x \cdot (C_3H_6O_3)_n$ wherein n represents a number from 4 to 12 and x corresponds to the valence of the metal M, and are useful in the food industry as substitutes for liquid lactic acids in the making of bread and beverages.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–6 and 10 are cancelled.

Claims 7–9, 11 and 12 are determined to be patentable as amended.

New claim 13 is added and determined to be patentable.

7. A process according to claim [6] *13* in which the aqueous solution of lactic acid comprises a hydrolized aqueous solution containing lactic acid content of 20 to 30% by weight.

8. A process according to claim [5] *13* in which the metal compound is selected from the group consisting of oxides, hydroxides, carbonates and neutral lactates.

9. A process according to claim [5] *13* in which the metal compound is selected from the group consisting of calciumoxide, calciumhydroxide, calciumcarbonate, calciumlactate, calciumtrilactate and calciumtetralactate.

11. A process according to claim [10] *18* in which evaporation occurs at a temperature of from 60° to 80° C.

12. A process according to claim [10] *13* in which evaporation occurs within a thin film apparatus or drum dryer under vacuum.

*13. A process for the production of hyperacidic, nonhygroscopic, noncaking, free-flowing, water-soluble, dry, solid metal lactates comprising:*

(a) *heating a dilute aqueous solution of lactic acid having a maximum concentration of 50% for a sufficient period of time to hydrolyze the lactic acid esters therein and to reduce the residual polylactic acid content thereof to a maximum amount of 0.5% 8c by weight of said solution;*

(b) *reacting x plus n moles of said dilute solution with one mole of a metal compound selected from the group consisting of compounds of lithium and alkaline earth metals in a quantity corresponding stoichiometrically to the desired hyperacidic metal lactate to be formed; and*

(c) *removing the water solvent by drying the reaction product in a vacuum of 10 to 50 TORR and at a temperature of from 40° C. to 90° C. in the shortest possible time to produce said hyperacidic solid metal lactate having the formula $M\ (C_3H_5O_3)_x\ (C_3H_6O_3)_n$ wherein n is a number from 4 to 12 and x corresponds to the equivalence of the metal M, said solid metal lactate having a melting point within the range of from about 133° C. to about 149° C.*

* * * * *